United States Patent
Cielo

(10) Patent No.: US 7,622,103 B1
(45) Date of Patent: Nov. 24, 2009

(54) HAIR AND SCALP TOXIN REMOVER COMPOSITION AND METHOD OF ITS MAKING

(76) Inventor: Jill M. Cielo, 2055 53rd Ave., Vero Beach, FL (US) 32966

( * ) Notice: Subject to any disclaimer, the term of this patent is extended or adjusted under 35 U.S.C. 154(b) by 885 days.

(21) Appl. No.: 10/811,644

(22) Filed: Mar. 29, 2004

Related U.S. Application Data

(60) Provisional application No. 60/458,076, filed on Mar. 27, 2003.

(51) Int. Cl.
- *A61K 8/00* (2006.01)
- *A61K 8/18* (2006.01)
- *A61K 8/19* (2006.01)
- *A61K 8/64* (2006.01)

(52) U.S. Cl. ............ 424/70.1; 424/70.2; 424/70.4; 424/70.5

(58) Field of Classification Search ............ None
See application file for complete search history.

(56) References Cited

U.S. PATENT DOCUMENTS

| | | | | |
|---|---|---|---|---|
| 3,652,399 | A | 3/1972 | Isono | 195/52 |
| 4,152,418 | A | 5/1979 | Pader | 424/50 |
| 4,873,079 | A | 10/1989 | Hahn et al. | 424/70 |
| 4,959,179 | A | 9/1990 | Aronson et al. | 242/135 |
| 5,078,990 | A | 1/1992 | Martin et al. | 424/70 |
| 5,089,414 | A | 2/1992 | Christner et al. | 435/265 |
| 5,976,555 | A * | 11/1999 | Liu et al. | 424/401 |
| 6,030,948 | A | 2/2000 | Mann | 514/12 |
| 6,376,557 | B1 * | 4/2002 | Zaveri | 424/725 |
| 6,410,005 | B1 | 6/2002 | Galleguillos et al. | 424/70 |
| 6,491,902 | B2 | 12/2002 | Shefer et al. | 424/70.1 |
| 2002/0119174 | A1 * | 8/2002 | Gardlik et al. | 424/401 |
| 2003/0007941 | A1 * | 1/2003 | Cornelius et al. | 424/70.1 |

FOREIGN PATENT DOCUMENTS

WO   WO 9625943 A1 * 8/1996

OTHER PUBLICATIONS

Wikipedia, "Proteases".*
Wikipedia, "Lipases".*
Maggie Greenwood—Robinson, Ph.D., *hair savers for women*, Three Rivers Press, 2000, pp. 28-31.
Trionics Systems Inc. website, http://kpbsbeauty.com/trionics.htm, as printed Mar. 25, 2004, p. 1-4.

* cited by examiner

*Primary Examiner*—Isis A Ghali
(74) *Attorney, Agent, or Firm*—Brian S. Steinberger; Law Offices of Brian S. Steinberger, P.A.

(57) ABSTRACT

A novel hair treatment formula and method of making and using that reduces hair loss and extends the life of existing hair. The treatment cleanses the hair and scalp of excessive oils, wastes, waxes, dirts, dust, trace minerals, and toxins due to medications, stress, hormones, trauma, poor diet, and the like. The treatment also effectively removes foreign materials from the hair that can interfere with other products being used to perm, dye, condition or straighten the hair.

5 Claims, No Drawings

HAIR AND SCALP TOXIN REMOVER COMPOSITION AND METHOD OF ITS MAKING

This invention claims the benefit of priority from U.S. Provisional patent application 60/458,076 filed Mar. 27, 2003.

FIELD OF THE INVENTION

This invention relates to topical hair applications, and in particular to a novel hair treatment formula and methods of making and using the formula, for removing toxins or toxic deposits from the hair to reduce hair loss and extend the healthy life of existing hair.

BACKGROUND AND PRIOR ART

Hair loss for average adults usually results in some 40 to 100 hairs per day being lost from one's head. Additionally, medical wastes, toxins and traumatic events have been known to have disastrous effects on one's hair, and increase hair loss and are harmful to existing hair. The toxins that result in hair loss can also be caused by hormone changes, physical changes, emotional stress, and the like. Hair loss has been known to further increase as a result of chemotherapy, prescription drugs, dietary supplements, age, health conditions, and the like. See for example, Greenwood-Robinson, Maggie, *Hair Savers for Women, A Complete Guide to Preventing and Treating Hair Loss*, Three Rivers Press, New York, pages 28-31, 2000.

Several patents disclose hair and scalp treatments with formulations that individually include some, but not all, of the ingredients used in the present invention. For example, U.S. Pat. No. 6,030,948 to Mann discloses a hair regeneration composition containing: water, sodium laureth sulfate, cocamidopropyl betaine, tetrasodium EDTA, alkyloxypolyethyleneoxyethanol, propylene glycol and fragrance. U.S. Pat. No. 6,410,005 B1 to Galleguillos discloses a polymeric hair-styling composition with disodium oleamide sulfosuccinate as an ingredient. U.S. Pat. No. 5,362,486 describes propylene glycol as a suitable solvent for a hair setting lotion.

Components such as tall oil, methylparaben, propylparaben and cocamidopropyl betaine are ingredients used for hair preparations in U.S. Pat. No. 4,873,079 to Hahn et al. for a hair coloring product, and U.S. Pat. No. 6,491,902 B2 to Shefer et al., for a controlled delivery system in hair care products.

Ammonium lauryl sulfate is a shampoo and conditioner ingredient in U.S. Pat. No. 5,078,990 to Martin et al. In 1972, U.S. Pat. No. 3,652,399 disclosed the use of alkaline protease in formulations of detergent and other cleanser compositions for cloth, hair, kitchen surfaces and the like.

Hair product formulations identified in a Mar. 25, 2004 search of beauty supply websites on the Internet identified several products containing enzymes and identified products manufactured by Trionics Systems, Inc., College Park, N.Y. The enzyme formulations are used as color developers, thickeners, texturizers, moisturizers, volumizers and to enhance waving of hair. None of the formulations mention specific enzymes nor use to reduce hair loss.

None of the references cited above, address the specific problem of removing toxins from hair to reduce hair loss, nor does any individual reference combine all of the formula ingredients of the present invention.

SUMMARY OF THE INVENTION

The first objective of the present invention is to provide a hair treatment formula and method of making and using for reducing hair loss characterized as telogen effluvium and all variations of telogen effluvium such as, but not limited to, sudden, delayed, chronic and non-chronic.

The second objective of the present invention is to provide a hair treatment formula and method of making and using to reduce hair loss known as androgenetic effluvium.

The third objective of the present invention is to provide a hair treatment formula and method of making and using for extending the life of existing hair.

The fourth objective of the present invention is to provide a hair treatment formula and method of making and using for removing toxins and toxic byproducts from drugs and other medications from one's hair.

The fifth objective of the present invention is to provide a hair treatment formula and method of making and using to effectively reduce hair loss side effects caused by interferon drug treatment of hepatitis patients.

The sixth objective of the present invention is to provide a hair treatment formula and method of making and using for removing foreign materials from hair to ensure maximum effectiveness of other hair treatments.

A preferred embodiment of the formula of the present invention includes water, ammonium lauryl sulfate, sodium laureth sulfate, disodium oleamide MEA sulfosuccinate, cocamide DEA, cocamidopropyl betaine, alkyloxypolyethylene-oxyethanol, tall oil MEA and tetrasodium ethylenediaminetetraacetic acid (EDTA), propylene glycol, diazolidinyl urea, methylparaben, propylparaben, sodium bisulfate, fragrance, sodium chloride, mixed proteases.

A preferred method of making includes filling a mixing vessel having a variable-speed propeller mixer, with the amount of water specified in the formula, then adding each ingredient in the formula in the order and amount listed in Table 1 below, beginning with ammonium lauryl sulfate. The ingredients are mixed thoroughly between each ingredient addition to insure uniformity. The mixing occurs at room temperature or slightly higher temperatures.

Further objects and advantages of this invention will be apparent from the following detailed description of the presently preferred embodiments, which are explained in tables, examples and the discussion below.

DESCRIPTION OF THE PREFERRED EMBODIMENTS

Before explaining the disclosed embodiments of the present invention in detail it is to be understood that the invention is not limited in its application to the details of the particular arrangement shown since the invention is capable of other embodiments. Also, the terminology used herein is for the purpose of description and not of limitation.

A preferred embodiment of the novel formula is an effective treatment for hair loss known as telogen effluvium, a condition first described by Kligman in 1961, as sudden diffuse hair loss likely caused by external factors that result in a disruption of the normal cycle of hair growth. Subsequent to 1961, there have been several added classifications of telogen effluvium, including sudden, delayed, chronic and non-chronic.

Hair life cycles include periods of growth (anagenic phase), cessation of growth (catagenic phase), and resting/loss (telogenic phase). It is telogen hairs that are found in the environment on a regular basis because hair loss is a natural phenomenon. Hairs are typically shed during shampooing, combing or brushing, at a rate of less than 100 per day. If a significant number of hair follicles simultaneously enter the telogenic or resting phase, the clinical result is likely to be telogen effluvium, including further characterizations as sudden, delayed, chronic or non-chronic.

In other conditions such as androgenetic effluvium, you see an increase in the number of hairs in the telogenic phase over a period of years, instead of months. Telogen effluvium is the shedding of hairs that have been prematurely pushed from the anagen (growth) phase into the telogen (resting) phase. Anagen hairs are firmly attached at the roots, whereas, telogen hairs are loosely attached and hence fall out easily. This sudden abnormal change in hair growth dynamics can be temporary and may be precipitated by illness, childbirth, drugs, stress, crash dieting or other traumatic events. Even though the hair loss condition can be temporary, it is desirable to have a product that can reduce the heartbreak of sudden, excessive hair thinning and loss.

The discussion below begins with the novel formula for reducing hair loss from the causes stated above, and then proceeds to methods for making and using the formula.

A preferred embodiment of the novel formula is described in Table 1.

TABLE 1

FORMULA

| Ingredients | Recommended Range in percent (%) |
| --- | --- |
| Water | approximately 71.00-approximately 93.00 |
| Ammonium Lauryl Sulfate | approximately 1.00-approximately 5.00 |
| Sodium Laureth Sulfate(and) Disodium Oleamide MEA Sulfosuccinate (and) Cocamide DEA (and) Cocamidopropyl Betaine | approximately 5.00-approximately 10.00 |
| Alkyloxypolyethyleneoxyethanol (and) Tall Oil MEA (and) Tetrasodium EDTA | approximately .50-approximately 5.00 |
| Cocamidopropyl Betaine | approximately .10-approximately 2.00 |
| Propylene Glycol (and) Diazolidinyl Urea (and) Methylparaben (and) Propylparaben | approximately .50-approximately 1.00 |
| Sodium Bisulfate | approximately 0.01-approximately 1.00 |
| Tetrasodium ($_{ethylenediaminetetraacetic\ acid}$) EDTA | approximately 0.01-approximately 2.00 |
| Fragrance | approximately 0.01-approximately 1.00 |
| Sodium Chloride | approximately 0.01-approximately 1.00 |
| Mixed Proteases | approximately 0.01-approximately 1.00 |

The above ingredients are shown in weight percent, and are available from commercial suppliers such as Brooks, Sigma (St. Louis, Mo.) and Aldrich (Milwaukee, Wis.).

Except for Mixed Proteases, all other ingredients listed in Table 1 are available by the chemical or common name listed. Mixed Proteases is a mixture of enzymes, primarily lipase and protease. The mixture of enzymes can be the same or similar to those disclosed in U.S. Pat. Nos. 4,152,418 to Pader; 4,959,179 to Aronson et al. and 5,089,414 to Christner and incorporated herein by reference. For example, Pader '418 discloses Protease, Lipase, Bromelain, Papain and Trypsin, as mixed enzymes. The enzyme mixture is the active ingredient of the present invention and is the right combination of enzymes that function to remove toxins that can cause hair loss.

The enzyme mixture functions as a natural catalyst. Natural enzymes are specialized proteins selected from certain cells of living organisms that isolate certain chemical reactions without taking part in them. Thus, the enzyme mixture of the present invention combines the appropriate enzymes to effectively remove harmful substances or toxins that lead to hair loss characterized as telogen effluvium or androgenetic effluvium.

The formula ingredients in Table 1 mixed according to the process of manufacture, as follows: First, the water is charged into a mixing vessel with a variable-speed propeller mixer. Next, the ingredients are added to the mixing vessel in the order listed in Table 1, beginning with ammonium lauryl sulfate as the first ingredient added to the water in the mixing vessel. Ingredients are mixed well between each addition to insure uniformity. The mixing occurs at room temperature, which can be within a range from approximately 18° C. to approximately 30° C. The finished formula is a clear, transparent liquid with the consistency of a thin syrup, such as natural maple syrup.

The novel invention can be applied to the hair and scalp in several easy steps. First, wet hair with warm water. Then, apply the formula treatment in a modest amount, for example approximately one teaspoon to approximately one tablespoon. It is appropriate to vary the amount of formula used based on length and thickness of the hair being treated. Next, the treatment can be massaged into the hair and scalp, and then rinsed off. In cases where the hair has excess chlorine, metallic residue, medicines, oils, wax or lacquer, the treatment should be left in the hair for approximately 5 minutes, after which it is rinsed out. The treatment can be repeated as necessary. It is preferable that the treatment be given daily. After each treatment, conditioners can be applied and the hair styled, as usual.

Novel benefits include allowing the treatments to be used to prepare hair before treatments such as perms, dyes, conditionings and straightening by removing foreign materials from the hair. The foreign materials in the hair can interfere with the chemical compositions of the other products being used and can interfere with desired results. Cleansing the hair of foreign materials ensures the maximum effectiveness of other hair treatments.

The novel treatment strengthens the hair by removing obstructions from pore openings on the scalp where hardening, known as keratinization, occurs. Weak hair is commonly caused as a result of poorly keratinized hair. This can occur when an excess of material such as dust, dead skin and/or oils from sebaceous glands clog pore openings. These obstructions not only can create weak hair, but can also block pores empty of hair, preventing new growth.

The treatment effectively removes toxins from medications and drugs that travel through the blood stream and are deposited in the matrix or papilla of each hair. The deposit of toxins can lead to considerable amounts of hair loss if not removed. The treatment formula of the present invention eliminate traces of toxins or poisons from medications deep throughout the hair into the cortex and papilla, removing toxins deposited on the hair that would otherwise cause hair to be expelled from the head. The novel treatment extends longevity of healthy hair, and help stops negative side effects to other hair treatments.

Testing of the novel formula in March, 2003 has shown that hair loss can be reduced by up to approximately 50% or more (for example approximately 40 to approximately 100) over the usual 90-150 hair losses per day, which is the average that adults or consumers expect.

Further testing of the novel formula involved people with hepatitis C wherein interferon drugs are used for treatment. Usually there is no hair loss until about the 41st week of treatment. It was shown that after the 41st week, the patient was losing approximately 500 hairs per day. Treatment with the formula of the present invention was begun on a daily basis, and after the $8^{th}$ day of treatment, the hair loss was reduced to only approximately eight (8) hairs.

Cancer patients on chemotherapy drugs have reported similar results, when the patient is able to withstand daily cleansing of the hair; the hair loss is reduced by at least approximately 50% to approximately 95%.

It is of great commercial interest to provide a hair treatment product that can reduce the effects of hair loss caused by man's struggle to overcome disease and pollution of man's social, emotional and physical environment. Thus, the present invention is a formulation that can be used to reduce hair loss characterized as telogen effluvium and androgenetic effluvium; it can extend the life of existing hair; eliminate traces of toxins or poisons from medications deep throughout the hair into the cortex and papilla; remove toxins deposited on the hair that would otherwise cause hair to be expelled from the head; reduce the hair loss side effects of interferon drug treatment; and remove foreign materials from the hair, including waxes, dirt, dust, trace minerals, toxins due to stress, hormones, trauma, poor diet and the like.

The hair treatment formula of the present invention is also effective in removing foreign materials from the hair that can interfere with other products being used to perm, dye, condition or straighten the hair and is gentle enough to be useful in treating young children. It is also possible to use improve the overall health and well-being of a person being treated by the formula of the present invention, by removing harmful toxins and poisons from the hair.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A treatment formula composition for reducing hair loss and promoting hair life, consisting of:
   (a) 71.00% to 93.00%, by weight of Water;
   (b) 1.00% to 5.00%, by weight of Ammonium Lauryl Sulfate;
   (c) 5.00% to 10.00, by weight of a mixture of Sodium Laureth Sulfate and Disodium Oleamide MEA Sulfosuccinate and Cocamide DEA and Cocamidopropyl Betaine;
   (d) 0.50% to 5.00%, by weight of a mixture of Alkyloxypolyethyleneoxyethanol and Tall Oil MEA and Tetrasodium EDTA;
   (e) 0.10% to 2.00%, by weight of Cocamidopropyl Betaine;
   (f) 0.50% to 1.00%, by weight of a mixture of Propylene Glycol and Diazolidinyl Urea and Methylparaben and Propylparaben;
   (g) 0.01% to 1.00%, by weight of Sodium Bisulfate;
   (h) 0.01% to 2.00%, by weight of Tetrasodium EDTA;
   (i) 0.01% to 1.00%, by weight of Fragrance;
   (j) 0.01% to 1.00%, by weight of Sodium Chloride; and
   (j) 0.01% to 1.00%, by weight of an enzyme mixture, selected from the group consisting of: Protease, Lipase, Bromelain, Papain and Trypsin, wherein the formula treatment composition reduces hair loss and prolong hair life.

2. A method of preparing a treatment formula composition for reducing hair loss and promoting hair life, consisting of the steps of:
   (a) mixing 71.00% to 93.00%, water into a mixing vessel;
   (b) adding and mixing 1.00% to 5.00%, by weight of Ammonium Lauryl Sulfate with the water in the mixture vessel to form a first mixture;
   (c) adding and mixing 5.00% to 10.00, by weight of a mixture of Sodium Laureth Sulfate and Disodium Oleamide MEA Sulfosuccinate and Cocamide DEA and Cocamidopropyl Betaine to the first mixture to form a second mixture;
   (d) adding and mixing 0.50% to 5.00%, by weight of a mixture of Alkyloxypolyethyleneoxyethanol and Tall Oil MEA and Tetrasodium EDTA, to the second mixture to form a third mixture
   (e) adding and mixing 0.10% to 2.00%, by weight of Cocamidopropyl Betaine to the third mixture to form a fourth mixture;
   (f) adding and mixing 0.50% to 1.00%, by weight of a mixture of Propylene Glycol and Diazolidinyl Urea and Methylparaben and Propylparaben to the fourth mixture to form a fifth mixture;
   (g) adding and mixing 0.01% to 1.00%, by weight of Sodium Bisulfate to the fifth mixture to form a sixth mixture;
   (h) adding and mixing 0.01% to 2.00%, by weight of Tetrasodium EDTA to the sixth mixture to form a seventh mixture;
   (i) adding and mixing 0.01% to 1.00%, by weight of Fragrance to the seventh mixture to form an eighth mixture;
   (j) adding and mixing 0.01% to 1.00%, by weight of Sodium Chloride to the eighth mixture to form a ninth mixture; and
   (j) adding and mixing 0.01% to 1.00%, by weight of a mixed enzyme mixture, selected from the group consisting of: Protease, Lipase, Bromelain, Papain and Trypsin, to the ninth mixture to form the formula treatment composition, wherein the formula treatment composition reduces hair loss and prolong hair life.

3. The method of claim 2, wherein all the steps of adding and mixing are done at room temperature.

4. The method of claim 3, wherein the room temperature is between approximately 18 C to approximately 30 C.

5. The method of claim 4, further comprising the step of: mixing the formula treatment composition into a clear transparent liquid having the consistency of a thin syrup.

* * * * *